(12) United States Patent
Leier et al.

(10) Patent No.: US 10,617,587 B2
(45) Date of Patent: Apr. 14, 2020

(54) MASSAGE DEVICE FOR NECK PORTION

(71) Applicants: Expectations, LLC, Puyallup, WA (US); Beto Engineering & Marketing Co., Ltd., Taichung (TW)

(72) Inventors: Christopher Henry Leier, Taichung, WA (US); Lo Pin Wang, Taichung (TW)

(73) Assignee: Expectations, LLC, Puyallup, WA (US)

( * ) Notice: Subject to any disclaimer, the term of this patent is extended or adjusted under 35 U.S.C. 154(b) by 529 days.

(21) Appl. No.: 15/223,154

(22) Filed: Jul. 29, 2016

(65) Prior Publication Data

US 2018/0028388 A1   Feb. 1, 2018

(51) Int. Cl.
| | |
|---|---|
| *A61H 1/00* | (2006.01) |
| *A61H 9/00* | (2006.01) |
| *A61F 5/00* | (2006.01) |
| *A63B 26/00* | (2006.01) |

(52) U.S. Cl.
CPC .............. *A61H 1/003* (2013.01); *A61H 1/005* (2013.01); *A61H 9/0078* (2013.01); *A61H 9/0085* (2013.01); *A61F 5/00* (2013.01); *A61H 2201/0207* (2013.01);
(Continued)

(58) Field of Classification Search
CPC ........ A61H 1/003; A61H 1/005; A61H 1/066; A61H 1/008; A61H 1/02; A61H 1/0214; A61H 1/022; A61H 1/0292; A61H 1/0296; A61H 9/0028; A61H 2201/02; A61H 2201/0207; A61H 2201/021411; A61H 2201/1645; A61H 2201/1647; A61H 2201/1664; A61H 2201/1685; A61H 2205/04; A63B 23/12; A63B 23/1236; A63B 23/025; A63B 23/0211; A63B 26/00; A63B 21/0047; A63B 21/4029; A63B 21/4033; A63B 21/4037; A63B 21/4003; A63B 21/4039
See application file for complete search history.

(56) References Cited

U.S. PATENT DOCUMENTS 4,622,956 A * 11/1986 Nesheim ............ A61H 15/0092
                                                            601/119
8,100,846 B1 * 1/2012 LaMonica ............... A61F 5/048
                                                             128/845
(Continued)

FOREIGN PATENT DOCUMENTS

| CN | 203555937 U | 4/2014 |
|---|---|---|
| CN | 204182077 U | 3/2015 |
| CN | 105664441 A | 6/2016 |

*Primary Examiner* — Justine R Yu
*Assistant Examiner* — Matthew R Moon
(74) *Attorney, Agent, or Firm* — Charles E. Baxley (57) ABSTRACT

A massage device includes a rotatable member rotatably supported on a supporting base with a pivot axle, and a neck massage member engaged onto the rotatable member and rotated in concert with the rotatable member relative to the supporting base for engaging with a neck portion of a user and for exercising and massaging the neck portion of the user. The supporting base includes a number of rollers engaged with the rotatable member for rotatably supporting the rotatable member on the supporting base. The supporting base includes a number of sockets for engaging with and for supporting the rollers.

17 Claims, 12 Drawing Sheets

(52) U.S. Cl.
CPC ................ *A61H 2201/0214* (2013.01); *A61H 2201/0221* (2013.01); *A61H 2205/04* (2013.01); *A63B 26/00* (2013.01)

(56) References Cited

U.S. PATENT DOCUMENTS

| | | | | |
|---|---|---|---|---|
| 8,388,560 | B2* | 3/2013 | Jian | A61H 15/0092 |
| | | | | 601/118 |
| 8,480,543 | B1* | 7/2013 | Leier | A63B 23/025 |
| | | | | 482/51 |
| 8,764,693 | B1* | 7/2014 | Graham | A61F 5/042 |
| | | | | 5/636 |
| 8,932,322 | B2* | 1/2015 | Reynolds | A61H 23/02 |
| | | | | 606/201 |
| 2004/0243037 | A1 | 12/2004 | Zapalac et al. | |
| 2005/0015031 | A1 | 1/2005 | Lin | |
| 2006/0129072 | A1* | 6/2006 | Shin | A61H 7/004 |
| | | | | 601/18 |
| 2008/0086066 | A1 | 4/2008 | Munday | |
| 2009/0186751 | A1* | 7/2009 | Hauser | A63B 21/00047 |
| | | | | 482/141 |
| 2009/0298656 | A1* | 12/2009 | Dannenberg | A63B 22/14 |
| | | | | 482/141 |
| 2011/0137218 | A1* | 6/2011 | Collins | A61H 15/00 |
| | | | | 601/118 |
| 2015/0209612 | A1* | 7/2015 | Shen | A63B 21/068 |
| | | | | 482/147 |
| 2015/0352398 | A1* | 12/2015 | Chang | A63B 21/075 |
| | | | | 482/93 |
| 2016/0022531 | A1* | 1/2016 | Ryan | A61H 15/0092 |
| | | | | 601/131 |
| 2017/0202723 | A1* | 7/2017 | Serola | A47C 20/026 |

* cited by examiner

MASSAGE DEVICE FOR NECK PORTION

BACKGROUND OF THE INVENTION

1. Field of the Invention

The present invention relates to a massage device or mechanism, and more particularly to a massage device or mechanism including a massage pad or member rotatably supported on a supporting base for suitably exercising or massaging the neck portion of the user.

2. Description of the Prior Art

Various kinds of typical massage devices or mechanisms have been developed and provided for massaging various portions of the user, and normally comprise a resilient or soft massaging pad or member for softly contacting various portions of the user and for selectively exercising or massaging the various portions of the user when required.

For example, U.S. Patent Application No. 2008/0086066 to Munday discloses a typical inversion suspension exerciser comprising a massage device wherein massage members engage with grooves for attaching to the massage device and for selectively engaging with the user to selectively massage the user, and further teaches that the use of removable massage members allows for massage members of different sizes and shapes to be interchangeably attached in order to apply a desired amount of pressure to the user during the massage.

U.S. Patent Application No. 2004/0243037 to Zapalac et al. discloses a typical massage device comprising a plurality of massage members for engaging with and for massaging the user manually.

U.S. Patent Application No. 2005/0015031 to Lin discloses a further typical massage device comprising a plurality of rotatable massage members for engaging with and for massaging the user manually.

However, the typical massage devices may not be used for massaging the neck portion of the user, or the neck portion of the user may not be exercised with the typical massage devices.

The present invention has arisen to mitigate and/or obviate the afore-described disadvantages of the conventional massage devices or mechanisms.

SUMMARY OF THE INVENTION

The primary objective of the present invention is to provide a massage device or mechanism including a massage pad or member rotatably supported on a supporting base for suitably exercising or massaging the neck portion of the user.

In accordance with one aspect of the invention, there is provided a massage device comprising a supporting base, a rotatable member rotatably supported on the supporting base with a pivot axle for allowing the rotatable member to be rotated relative to the supporting base, the rotatable member including an upper portion, and a neck massage member engaged onto the rotatable member and rotated in concert with the rotatable member relative to the supporting base, for engaging with a neck portion of a user and for allowing the user to pivot or rotate and exercise and massage the neck portion of the user.

The supporting base includes a number of rollers disposed on the supporting base and engaged with the rotatable member for rotatably supporting the rotatable member on the supporting base. The supporting base includes a number of openings or sockets provided thereon for receiving and engaging with and for supporting the rollers respectively. The supporting base includes a peripheral flange extended therefrom, and the sockets are disposed on the peripheral flange and equally spaced from each other. The supporting base includes a number of pads attached to a bottom portion of the supporting base for frictionally contacting or engaging with the carrier or the ground or supporting table or the like.

The rotatable member includes a peripheral rib extended therefrom and contacted and engaged with the rollers for allowing the rotatable member to be rotatably supported on the supporting base. The supporting base includes a peripheral flange extended therefrom, the peripheral flange of the supporting base includes an outer diameter equal to that of the peripheral rib of the rotatable member for allowing the peripheral flange of the supporting base to be aligned with the peripheral rib of the rotatable member.

The rotatable member includes an opening formed in the upper portion of the rotatable member for receiving and engaging with the neck massage member. The neck massage member includes a container having a compartment formed in the container for receiving a fluid, such as a cold water or hot water. The neck massage member includes a lid for closing the compartment of the container and for stably retaining the fluid within the compartment of the container. The neck massage member includes a cover attached onto the container of the neck massage member for covering and protecting the container. The neck massage member includes two end caps attached to the container and contacted and engaged with the cover for positioning the cover on the container and for preventing the cover from being disengaged from the container.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
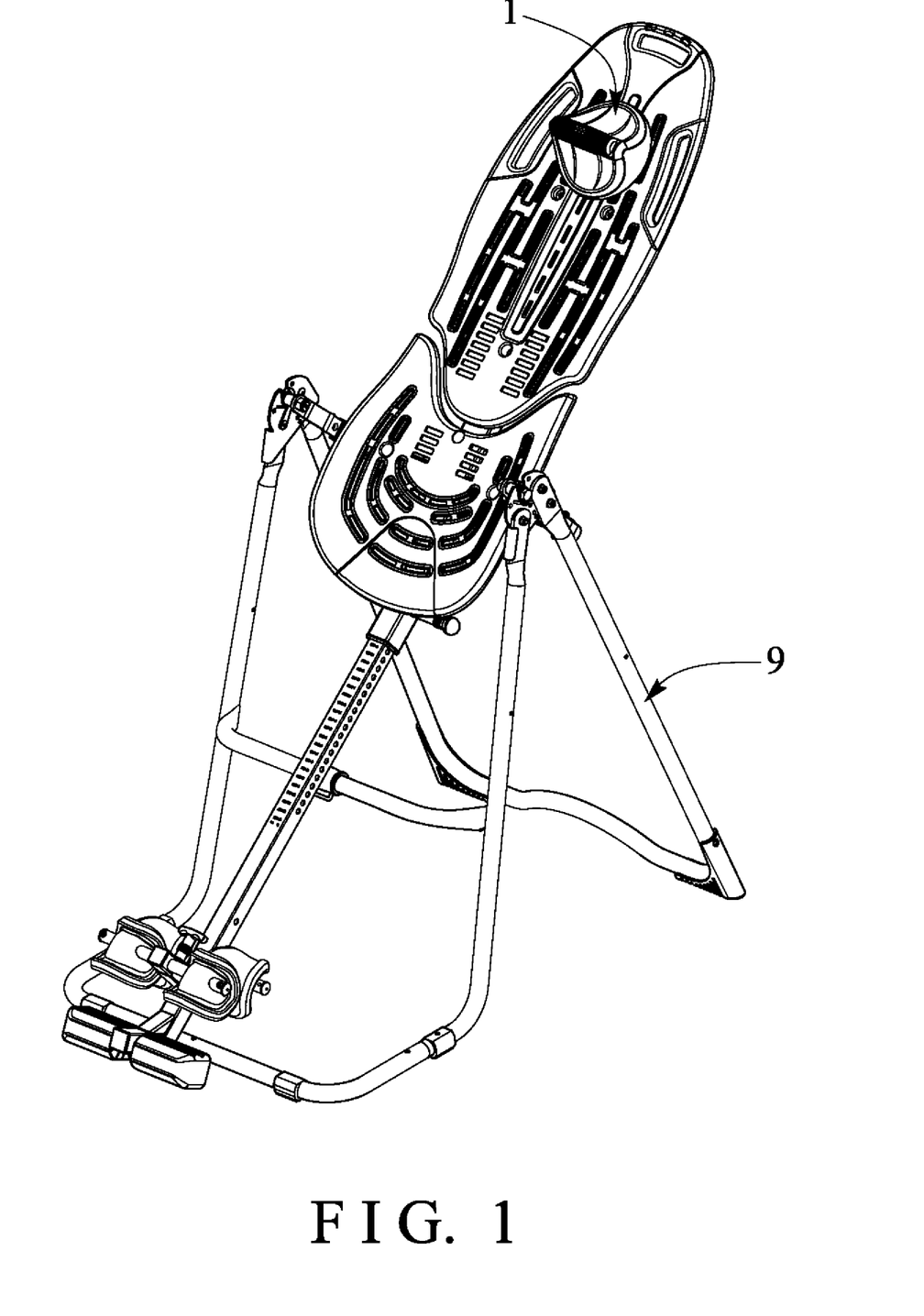
FIG. 1 is a perspective view of a massage device or mechanism in accordance with the present invention, illustrating the operation of the massage device or mechanism for attaching to a tilting inversion exerciser.
Figure 2:
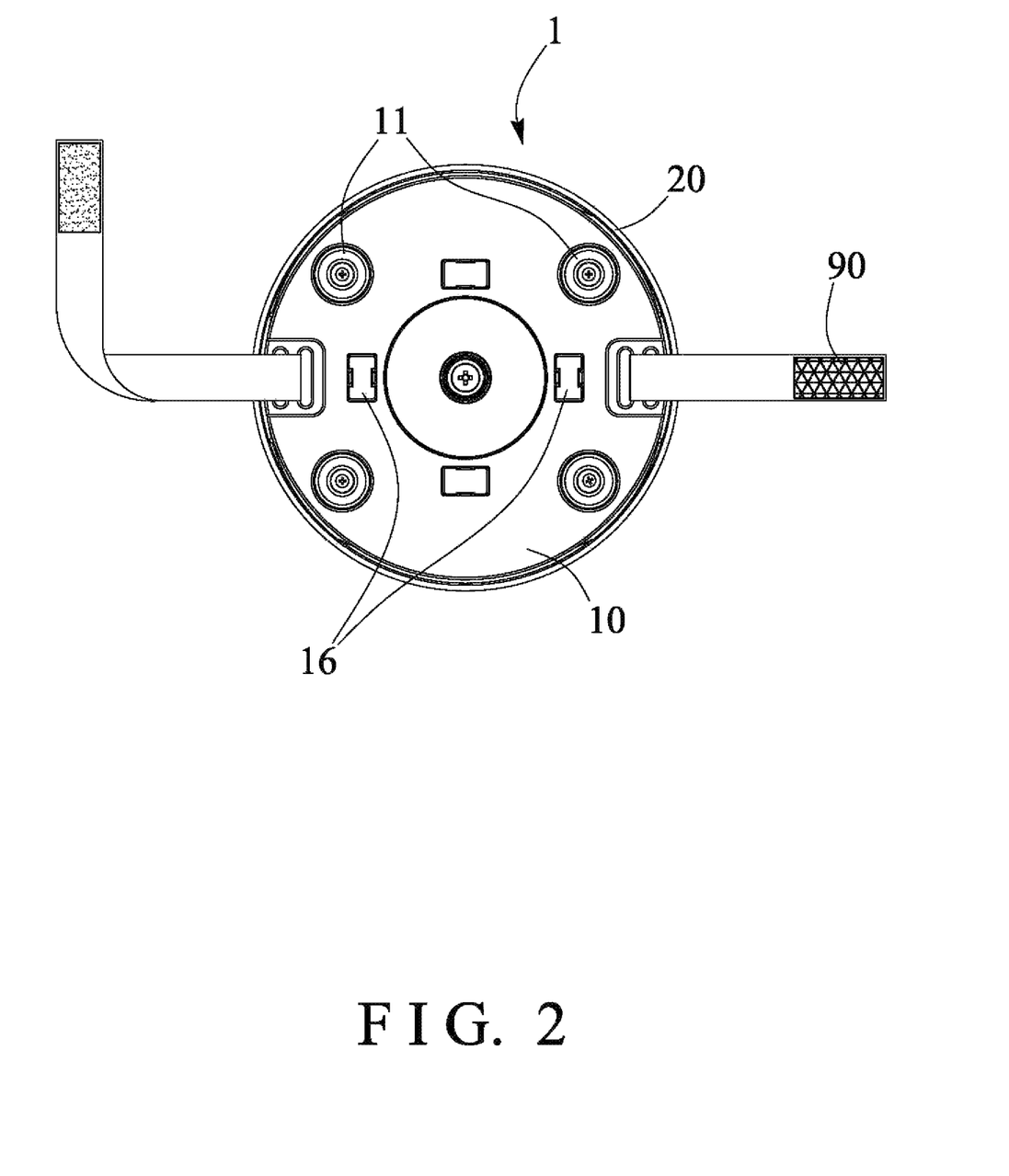
FIG. 2 is a bottom plan schematic view of the massage device or mechanism for the tilting inversion exerciser.
Figure 3:
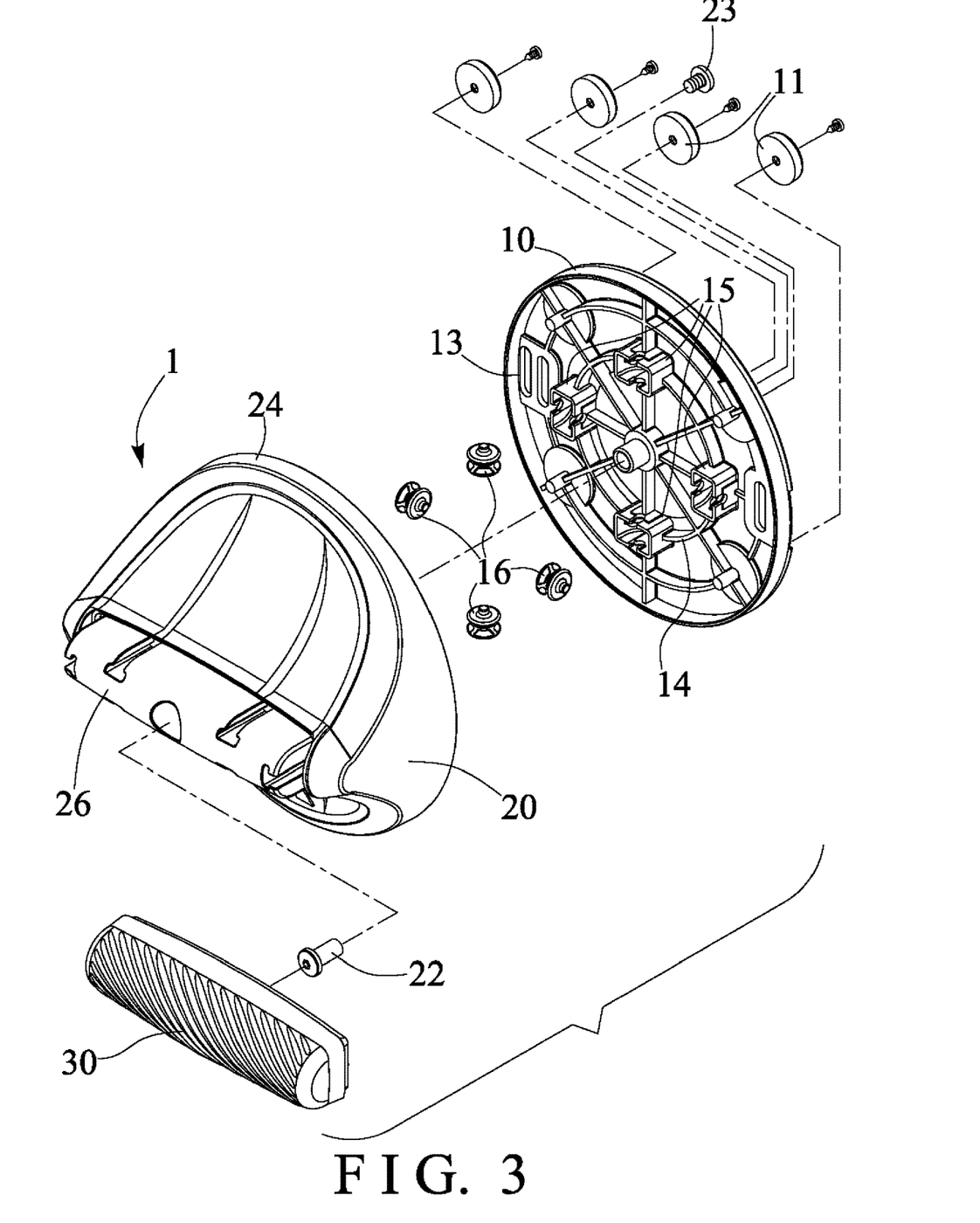
FIG. 3 is a partial exploded view of the massage device or mechanism as seen from the upper portion of the massage device or mechanism.
Figure 4:
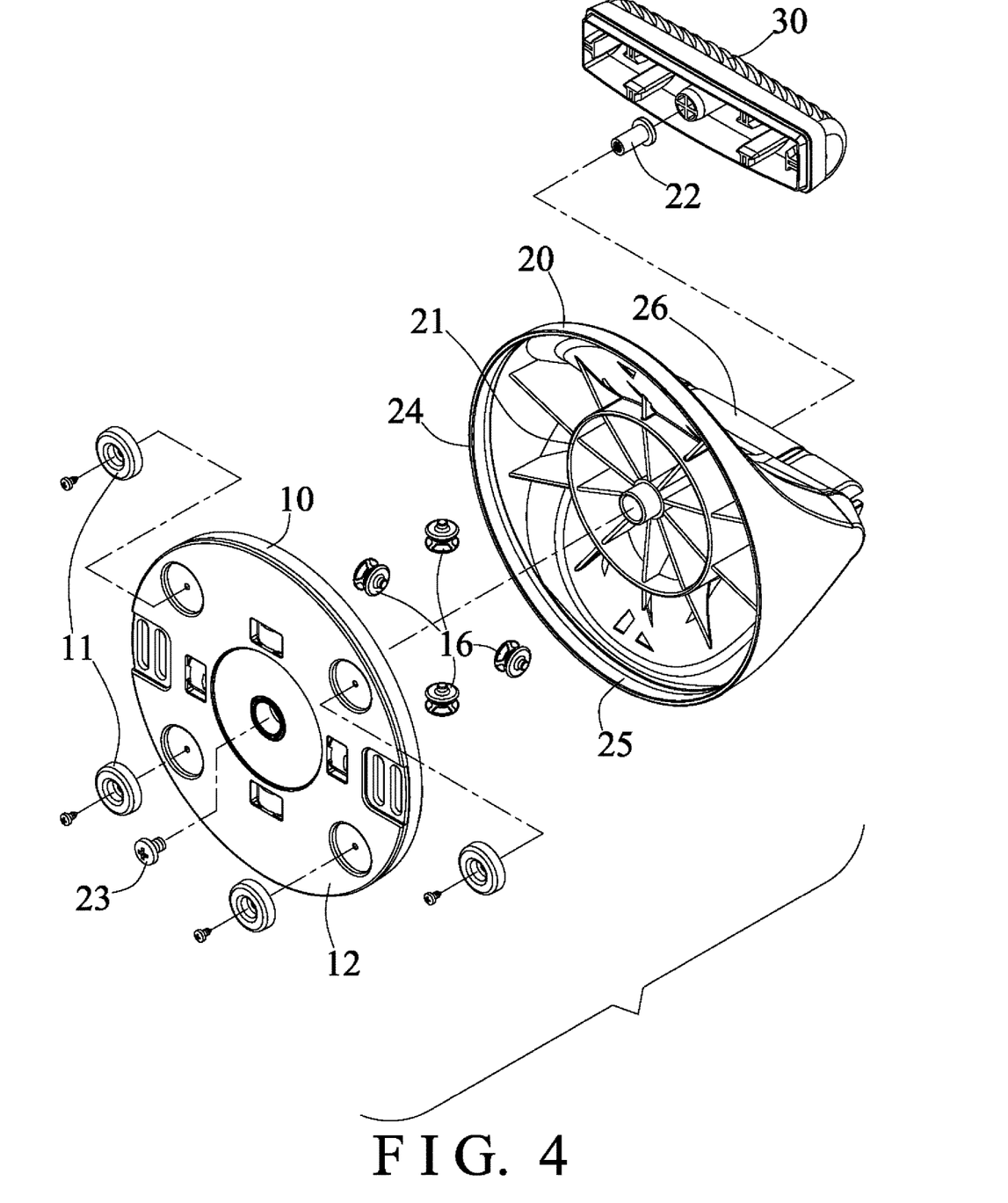
FIG. 4 is another partial exploded view of the massage device or mechanism as seen from the bottom portion of the massage device or mechanism.
Figure 5:
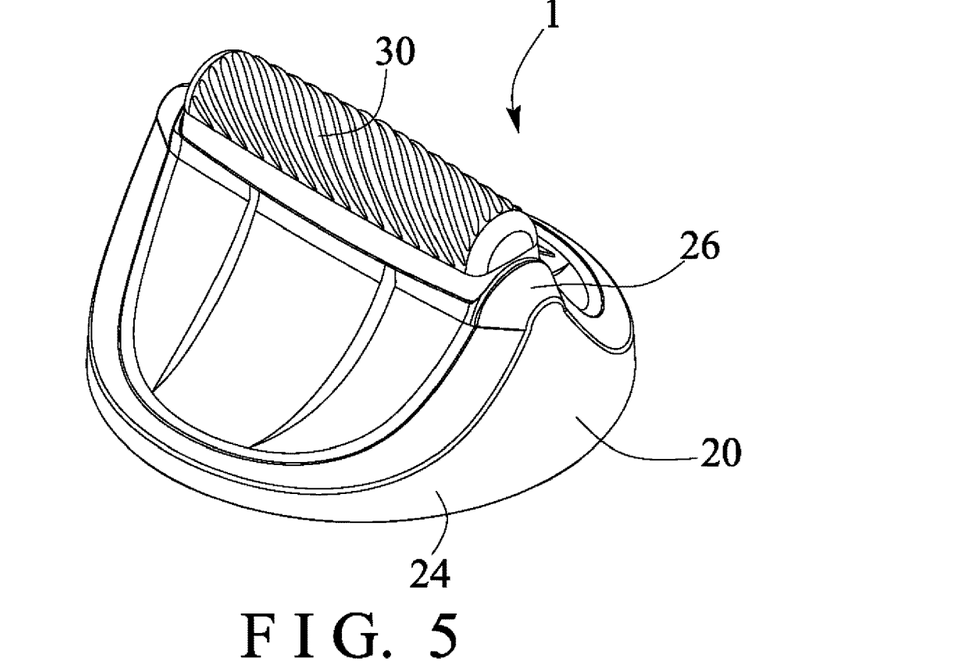
FIG. 5 is a perspective view of the massage device or mechanism.
Figure 6:
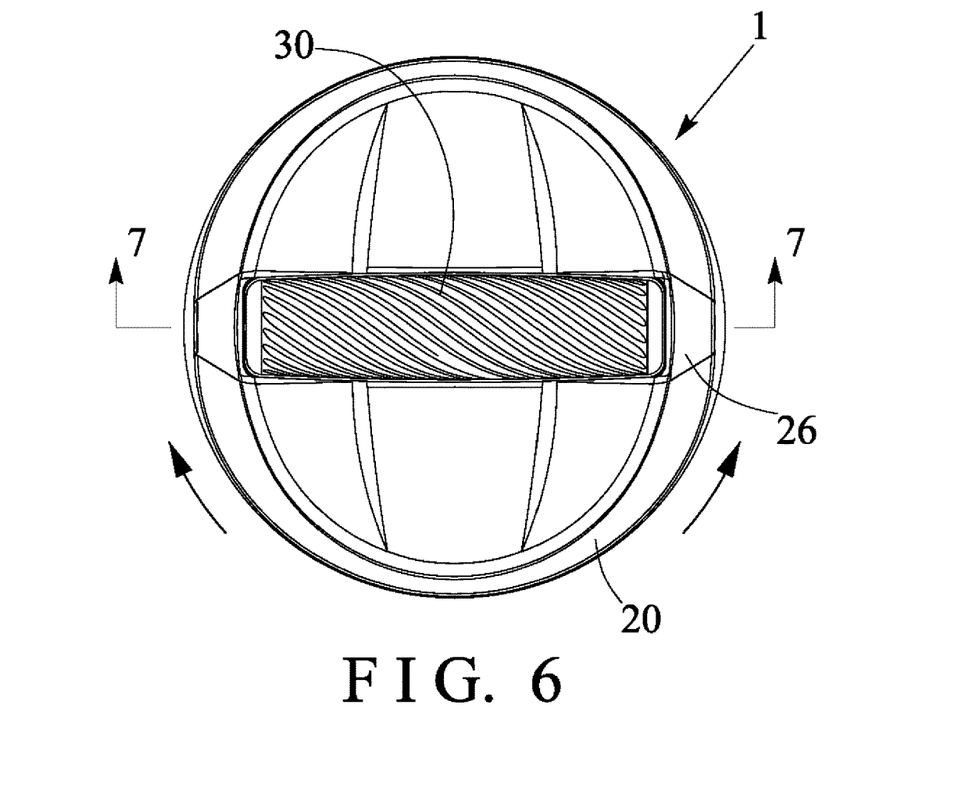
FIG. 6 is a top plan schematic view of the massage device or mechanism.

Referring to the drawings, and initially to FIGS. 1 and 2, a massage device or mechanism 1 in accordance with the present invention is provided for attaching or mounting or securing to a supporting base or carrier 9, such as a tilting inversion exerciser 9 or the like, with such as a fastening belt 90 or the like, or provided for being supported on a ground or supporting table 99 (FIG. 8) for suitably contacting or engaging with various portion, such as the neck portion 80 of the user 8 (FIGS. 8-10), and for suitably exercising or massaging the neck portion 80 of the user 8.

As shown in FIGS. 2-7, the massage device 1 comprises a lower supporting stand or base 10 for pivotally or rotatably attaching or mounting or securing or supporting a follower or rotatable member 20 thereon, the lower supporting base 10 includes one or more (such as four) stands or pads 11 disposed or attached to the lower or bottom portion 12 thereof, and the pads 11 are preferably manufactured or made of soft or resilient materials, such as plastic, rubber, or other synthetic materials or the like for frictionally contacting or engaging with the carrier 9, or the ground or supporting table 99.

The lower supporting base 10 includes an upper portion 13 having a circular or peripheral fence or flange 14 extended upwardly therefrom, and includes one or more (such as four) seats or sockets 15 formed or provided thereon (FIGS. 3, 7), such as disposed or provided on the peripheral flange 14 and equally spaced from each other, and one or more (such as four) pulleys or rollers 16 disposed or attached or mounted or secured to or in the sockets 15 respectively for contacting or engaging with the rotatable member 20 and for pivotally or rotatably supporting the rotatable member 20 thereon.

For example, the rotatable member 20 includes a circular or peripheral fence or rib 21 extended downwardly therefrom (FIGS. 3, 7) and having an outer diameter equal to that of the peripheral flange 14 of the supporting base 10 and contacted or engaged with the rollers 16 (FIG. 7) for allowing the rotatable member 20 to be pivotally or rotatably supported on the supporting base 10 and for allowing the rotatable member 20 to be smoothly pivoted or rotated relative to the supporting base 10. The rotatable member 20 may be pivotally or rotatably secured or coupled to the supporting base 10 with a pivot axle 22 and/or a fastener 23, for preventing the rotatable member 20 from being disengaged or separated from the supporting base 10.

Figure 7:
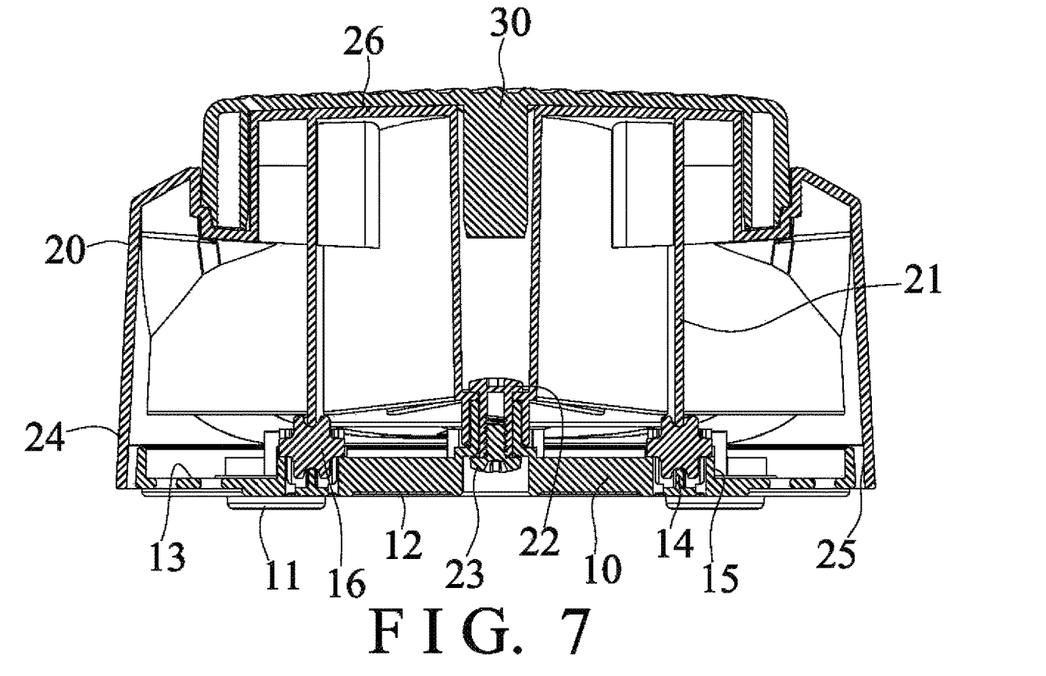
FIG. 7 is a cross sectional view of the massage device or mechanism taken along lines 7-7 of FIG. 6.

The rotatable member 20 includes a lower circular or peripheral fence or skirt 24 extended downwardly therefrom (FIGS. 4, 7) for forming or defining a compartment or chamber 25 therein and for receiving or accommodating or engaging with the supporting base 10 and for allowing the supporting base 10 to be suitably confined and shielded and protected within the chamber 25 of the rotatable member 20, best shown in FIG. 7. The rotatable member 20 includes an upper portion 26 having a relative upwardly converged and protruded and ridged structure or configuration for attaching or mounting or securing a neck massage member 30 thereon, and the neck massage member 30 may be made of softer or resilient materials for comfortably engaging with and supporting the upper or the neck portion 80 of the user 8 (FIGS. 8-10), and the neck massage member 30 may thus be pivoted or rotated in concert with each other relative to the supporting base 10.

Figure 8:
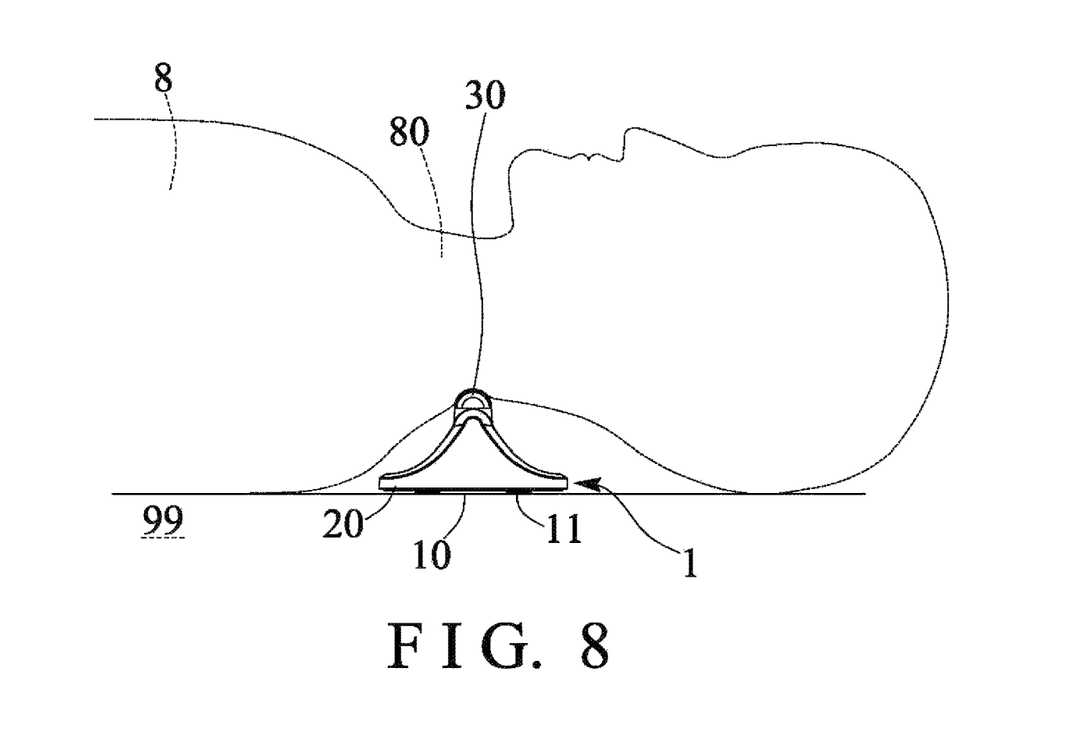
FIG. 8 is a top plan schematic view illustrating the operation of the massage device or mechanism.
Figure 9:
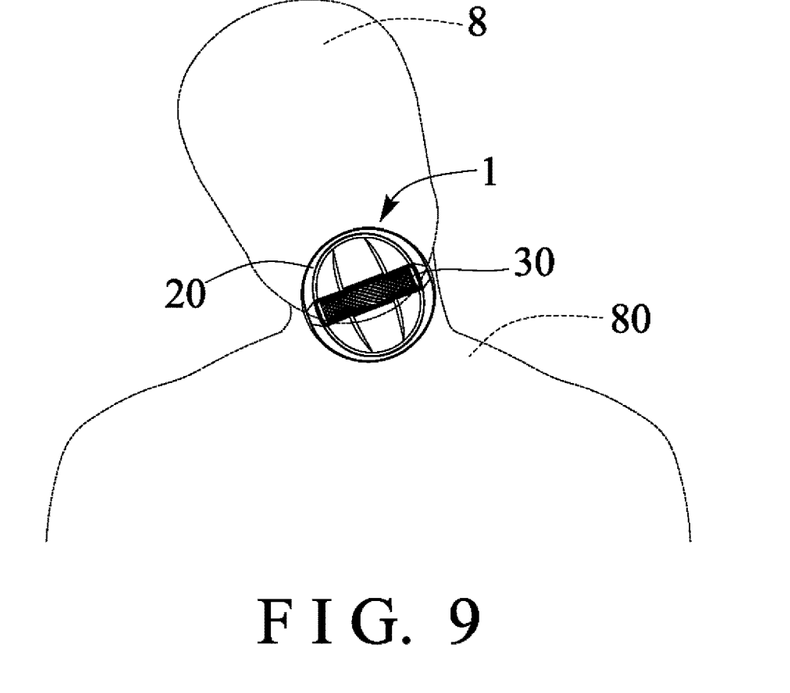
FIGS. 9, 10 are other top plan schematic views similar to FIG. 6, illustrating the operation of the massage device or mechanism.
Figure 10:
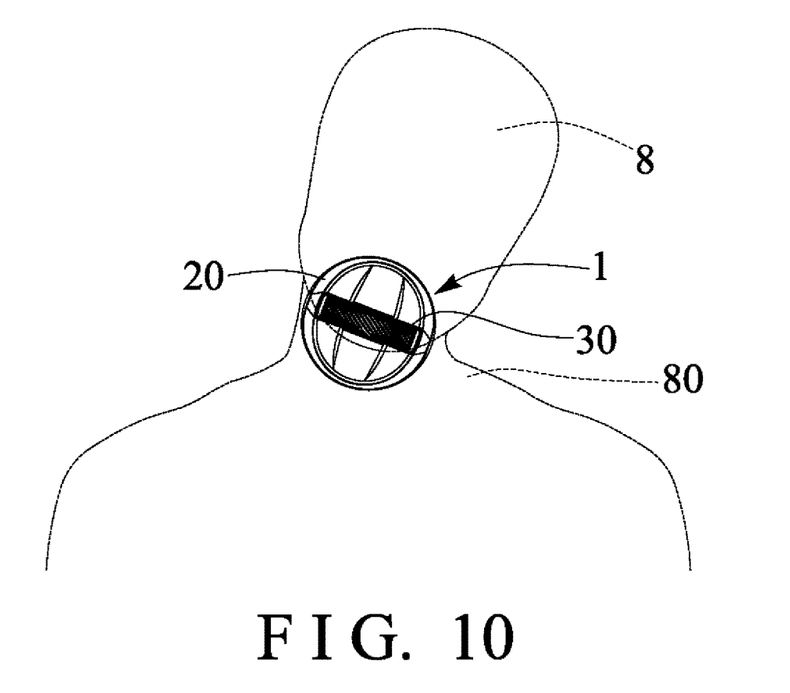

In operation, as shown in FIGS. 8-10, the neck portion 80 of the user 8 may be engaged with and supported on the neck massage member 30 of the rotatable member 20 which may be pivoted or rotated relative to the supporting base 10 in order to exercise or massage the neck portion 80 of the user 8. The neck massage member 30 of the rotatable member 20 is preferably manufactured or made of soft or resilient materials, such as plastic, rubber, or other synthetic materials or the like for resiliently or softly contacting or engaging with the neck portion 80 of the user 8. As shown in FIGS. 1-2, the massage device 1 may be attached or secured to the carrier or the tilting inversion exerciser 9 or the like, with the fastening belt 90 or the like for contacting or engaging with or massaging the neck portion 80 of the user 8.

Figure 11:
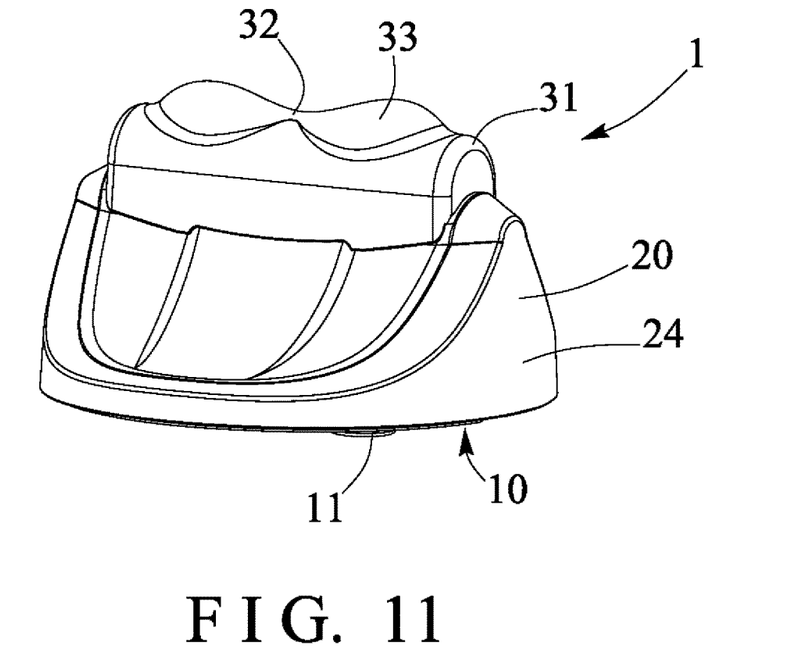
FIG. 11 is another perspective view similar to FIG. 5, illustrating the other arrangement of the massage device or mechanism.
Figure 12:
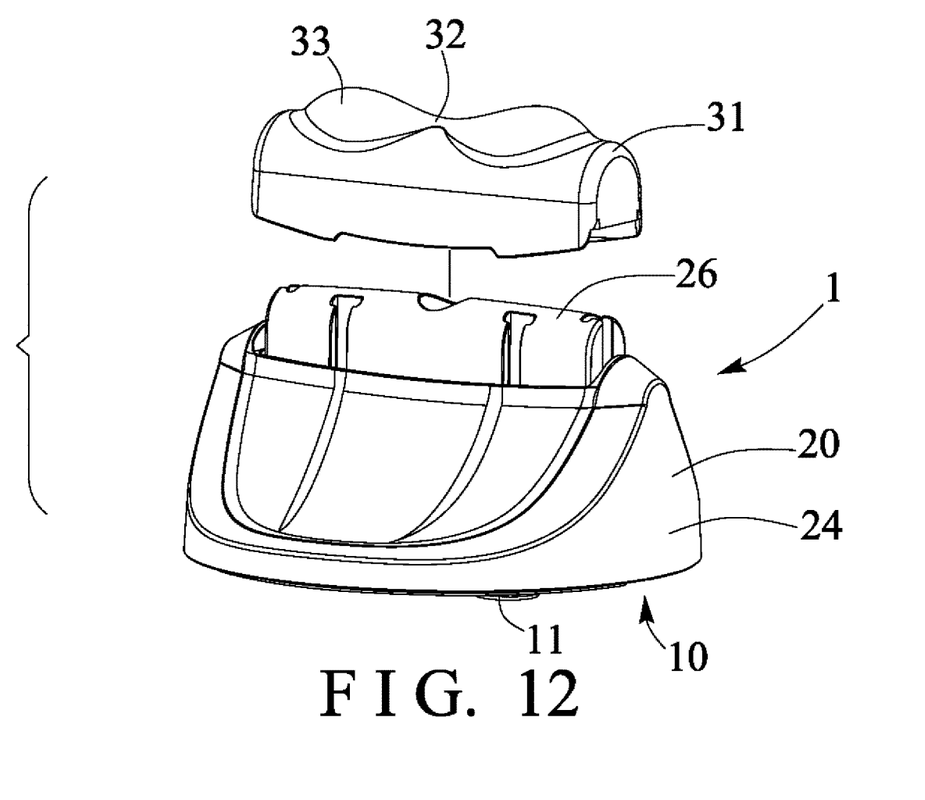
FIG. 12 is a partial exploded view of the massage device or mechanism as shown in FIG. 11.
Figure 13:
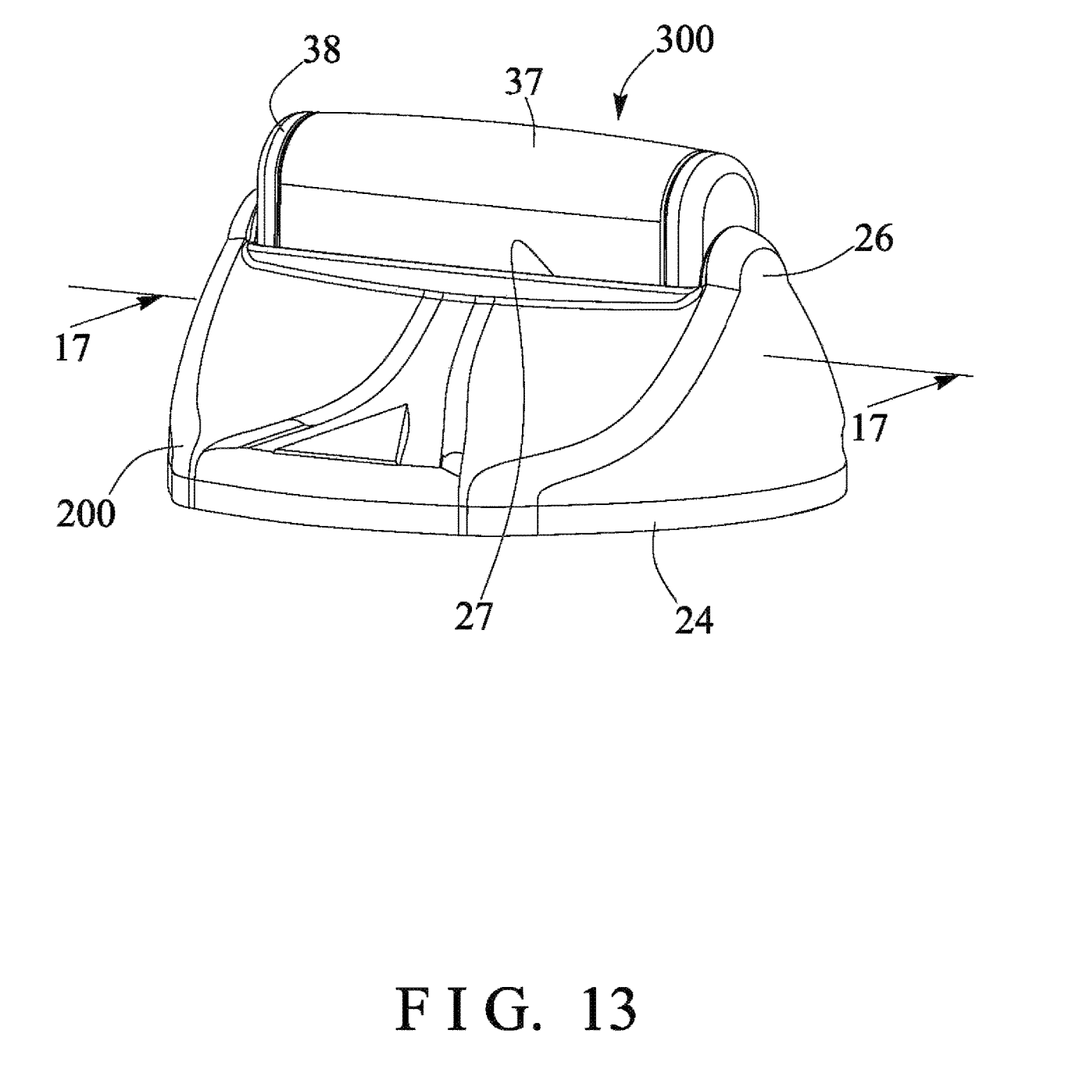
FIG. 13 is a further perspective view similar to FIGS. 5 and 11, illustrating the further arrangement of the massage device or mechanism.
Figure 14:
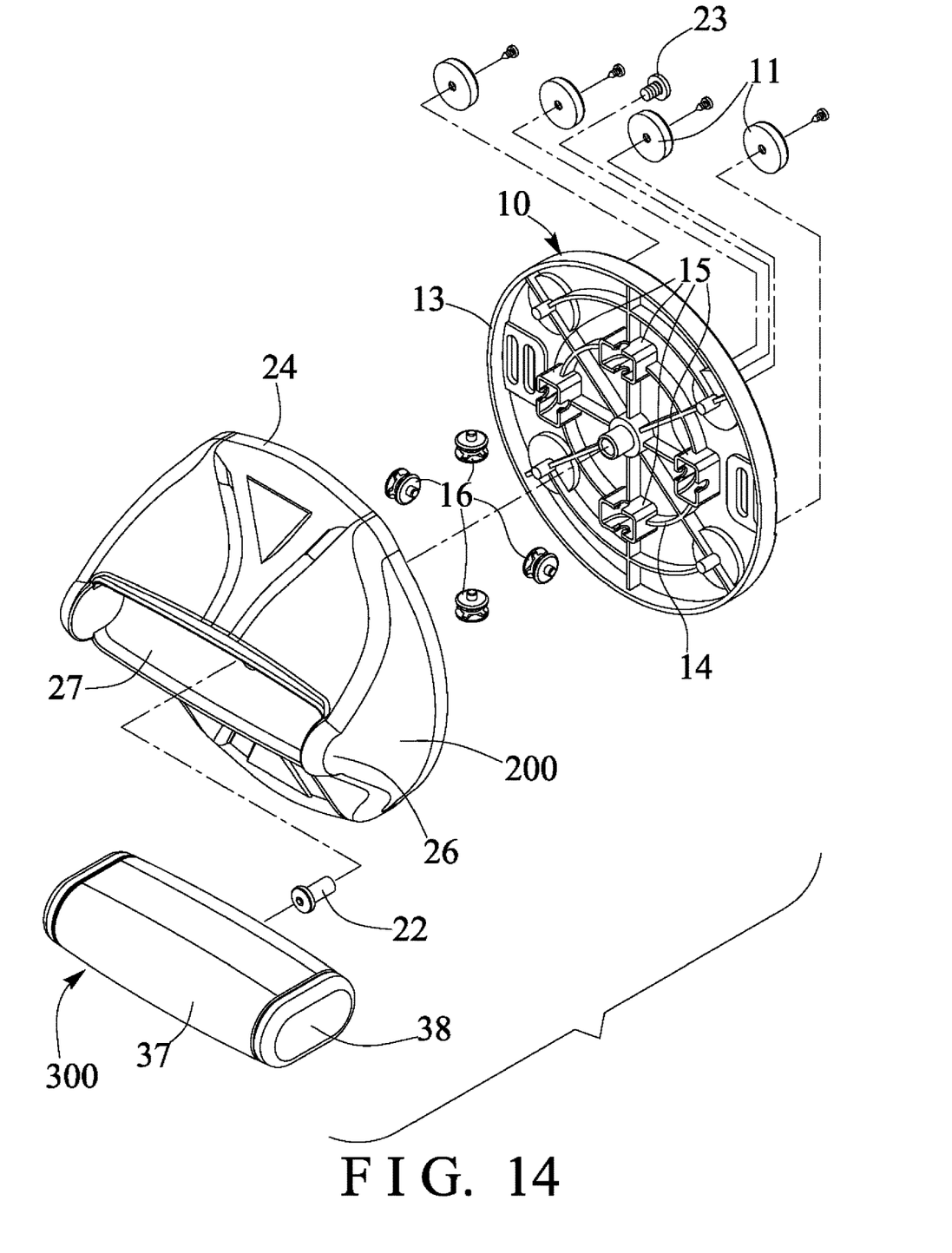
FIG. 14 is a partial exploded view of the massage device or mechanism as shown in FIG. 13, as seen from the upper portion of the massage device or mechanism.
Figure 15:
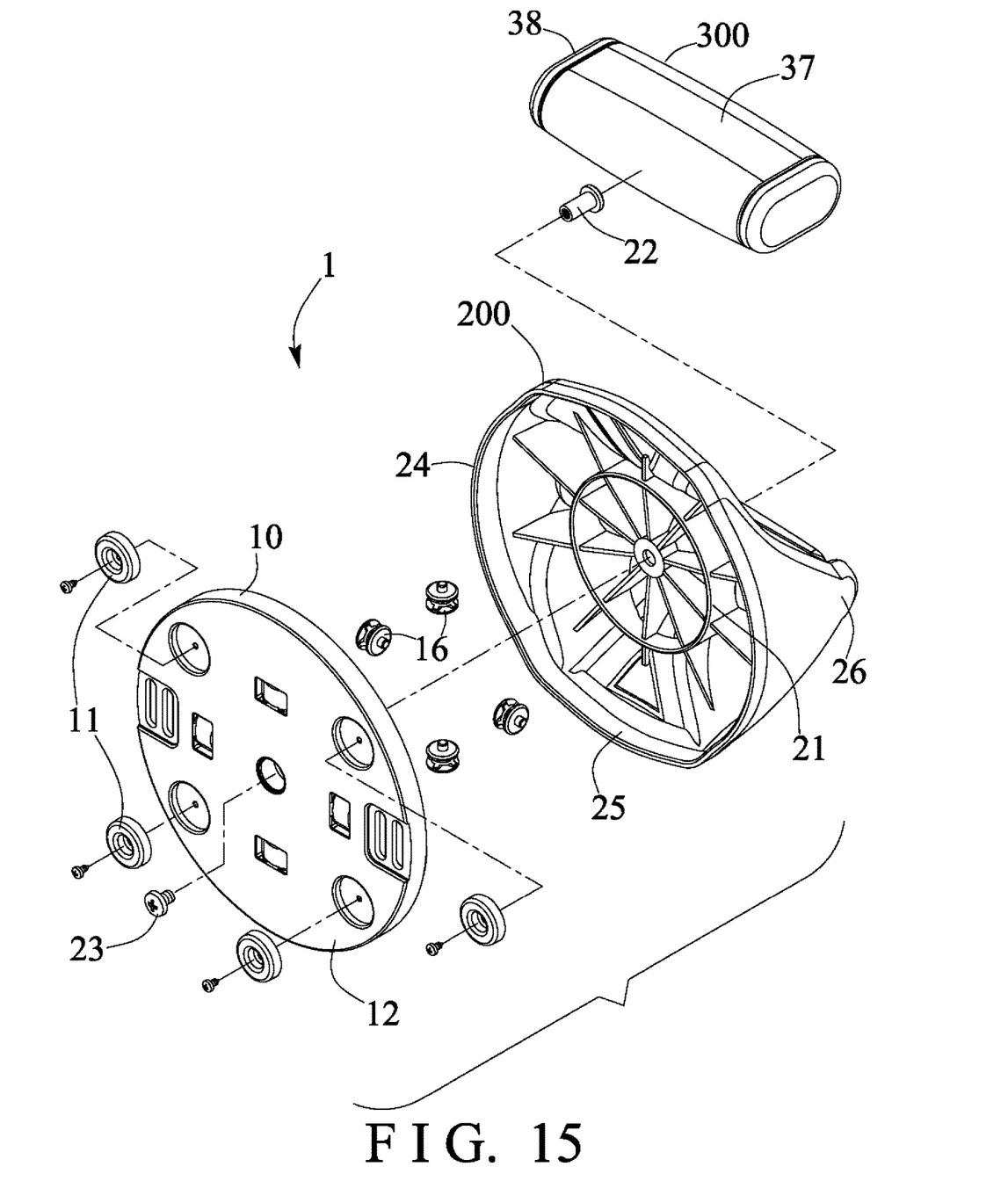
FIG. 15 is another partial exploded view of the massage device or mechanism as shown in FIGS. 13-14, as seen from the bottom portion of the massage device or mechanism.
Figure 16:
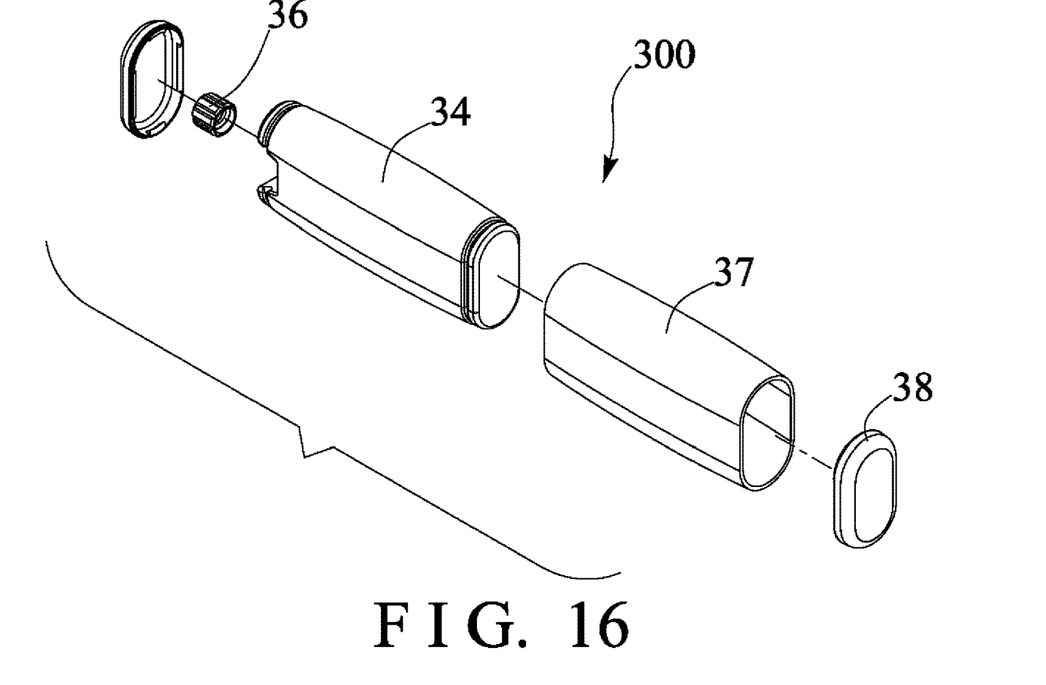
FIG. 16 is a further partial exploded view of the massage device or mechanism as shown in FIGS. 13-15.
Figure 17:
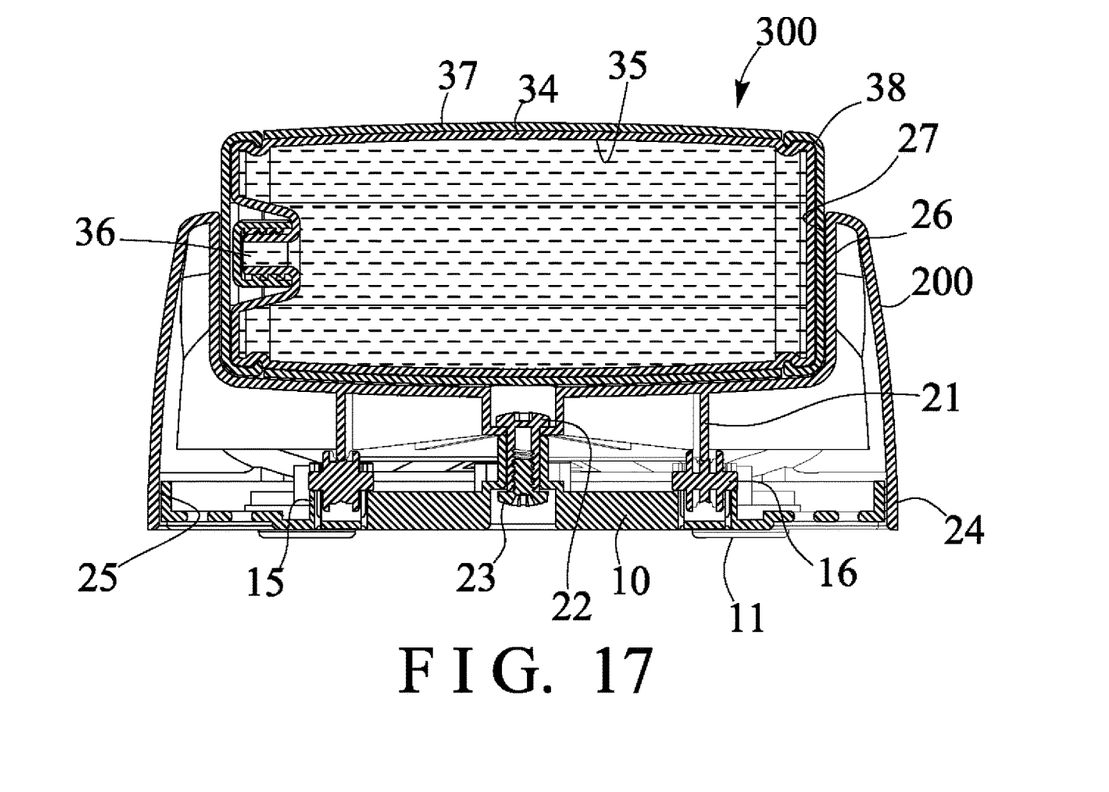
FIG. 17 is a cross sectional view of the massage device or mechanism as shown in FIGS. 13-16, taken along lines 17-17 of FIG. 13.

Alternatively, as shown in FIGS. 11-12, the neck massage member 31 may include a substantially U or V-shaped structure or configuration having a recess 32 formed or defined between two bulges or swellings 33 for solidly and stably receiving or engaging with or retaining the neck portion 80 of the user 8. Further alternatively, as shown in FIGS. 13-17, the rotatable member 200 includes a cavity or opening 27 formed in the upper portion 26 thereof for receiving or engaging with the neck massage member 300, in which the neck massage member 300 includes a bladder or container 34 having a chamber or compartment 35 therein for receiving or accommodating or engaging with a fluid, such as a cold or hot water or the like, and closable with a lid 36.

In operation, the cold or hot water or fluid contained in the compartment 35 of the container 34 of the neck massage member 300 may be used for cooling or heating the neck portion 80 of the user 8. The neck massage member 300 may further include an outer shield or cover 37 attached or mounted or secured onto the container 34 of the neck massage member 300 for covering or shielding and/or protecting the container 34 of the neck massage member 300, and one or more (such as two) end covers or caps 38 may further be provided and attached or mounted or secured onto the two end portions of the container 34 of the neck massage member 300 and contacted or engaged with the cover 37 for holding or retaining or positioning the cover 37 on the container 34 of the neck massage member 300 and for preventing the cover 37 from being disengaged or separated from the container 34 of the neck massage member 300.

Accordingly, the massage device or mechanism in accordance with the present invention includes a massage pad or member rotatably supported on a supporting base for suitably exercising or massaging the neck portion of the user.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

We claim:

1. A massage device comprising: a tilting inversion exerciser, a neck massage device having a supporting base mounted on the tilting inversion exerciser, the neck massager device comprising, a rotatable member rotatably supported on said supporting base with a pivot axle for allowing said rotatable member to be rotated relative to said supporting base in opposing first and second directions, said rotatable member including an upper portion, wherein said supporting base includes a plurality of rollers disposed on said supporting base and engaged with said rotatable member for rotatably supporting said rotatable member on said supporting base, and at least one neck massage member engaged onto said upper portion of said rotatable member and configured to be rotated in concert with said rotatable member relative to said supporting base in the opposing first and second directions, said neck massage member being selected from a group consisting of at least two different neck massage members having different neck engaging configurations, said neck massage member being interchangeable with at least one of the least two different neck massage members, said neck massage member and said rotatable member having a plane of rotation generally parallel to a bottom portion of the supporting base, said neck massage member configured to engage with a neck portion of a user and to exercise and massage the neck portion of the user, said neck massage member and said rotatable member configured to be rotatable with the user's neck portion in the opposing first and second directions.

2. The massage device as claimed in claim 1, wherein said supporting base includes a plurality of sockets provided thereon for receiving and engaging with said rollers respectively.

3. The massage device as claimed in claim 2, further comprising a peripheral flange extended from said supporting base, and said sockets being disposed on said peripheral flange and equally spaced from each other.

4. The massage device as claimed in claim 1, further comprising a plurality of pads attached to a bottom portion of said supporting base.

5. The massage device as claimed in claim 1, further comprising a peripheral rib extended from said rotatable member and contacted and engaged with said rollers for allowing said rotatable member to be rotatably supported on said supporting base.

6. The massage device as claimed in claim 5, further comprising a peripheral flange extended from said supporting base, said peripheral flange of said supporting base including an outer diameter equal to that of said peripheral rib of said rotatable member.

7. The massage device as claimed in claim 1, wherein said rotatable member includes an opening formed in said upper portion of said rotatable member for receiving and engaging with said neck massage member.

8. The massage device as claimed in claim 7 wherein said neck massage member includes a container having a compartment formed in said container for receiving a fluid, the fluid being selected from a group consisting of hot fluid and cold fluid.

9. The massage device as claimed in claim 8 wherein said neck massage member includes a lid for closing said compartment of said container.

10. The massage device as claimed in claim 8 wherein said neck massage member includes a cover attached onto said container of said neck massage member for covering and protecting said container.

11. The massage device as claimed in claim 10 wherein said neck massage member includes two end caps attached to said container and contacted and engaged with said cover for positioning said cover on said container and for preventing said cover from being disengaged from said container.

12. The massage device as claimed in claim 1, further comprising a fastening belt operatively connected to said supporting base.

13. The massage device as claimed in claim 1, wherein said neck massage member has a surface configured to engage the neck portion of the user selected from the group consisting of a contoured surface, a textured surface, a recess, a bulging, and a plurality of grooves.

14. The massage device as claimed in claim 1, wherein the neck massage member is made of a resilient material.

15. The massage device as claimed in claim 1, wherein said neck massage member includes a container and fluid disposed inside said container.

16. The massage device as claimed in claim 1, wherein at least one strap is configured to selectively interconnect the base and the tilting inversion exerciser.

17. The massage device as claimed in claim 1, wherein said neck massage member includes protrusions and said upper portion of said rotatable member includes slots configured and arranged to receive said protrusions thereby engaging said neck massage member onto said upper portion.

* * * * *